US008815597B2

(12) United States Patent
Chono et al.

(10) Patent No.: US 8,815,597 B2
(45) Date of Patent: Aug. 26, 2014

(54) BAGLIKE CONTAINER FOR CENTRIFUGATION AND METHOD OF GENE TRANSFER USING THE SAME

(75) Inventors: Hideto Chono, Otsu (JP); Junichi Mineno, Otsu (JP); Kazutoh Takesako, Otsu (JP); Takao Yoshida, Saitama (JP); Takashi Morimura, Saitama (JP); Kenji Sakai, Saitama (JP); Shin-ichi Yamada, Sakado (JP); Noritsugu Yabe, Sakado (JP); Yuko Taguchi, Sakado (JP)

(73) Assignee: Takara Bio Inc., Shiga (JP)

( * ) Notice: Subject to any disclaimer, the term of this patent is extended or adjusted under 35 U.S.C. 154(b) by 821 days.

(21) Appl. No.: 12/377,234

(22) PCT Filed: Aug. 23, 2007

(86) PCT No.: PCT/JP2007/066383
§ 371 (c)(1),
(2), (4) Date: Sep. 10, 2009

(87) PCT Pub. No.: WO2008/023770
PCT Pub. Date: Feb. 28, 2008

(65) Prior Publication Data
US 2010/0136680 A1  Jun. 3, 2010

(30) Foreign Application Priority Data
Aug. 23, 2006  (JP) .................................. 2006-227118

(51) Int. Cl.
| | | |
|---|---|---|
| *C12N 1/00* | (2006.01) | |
| *C12M 1/42* | (2006.01) | |
| *C12N 15/87* | (2006.01) | |
| *A61J 1/10* | (2006.01) | |
| *C12M 1/00* | (2006.01) | |
| *C12M 3/00* | (2006.01) | |
| *C12N 15/00* | (2006.01) | |
| *C12P 21/04* | (2006.01) | |
| *C12P 21/06* | (2006.01) | |
| *B01L 3/00* | (2006.01) | |

(52) U.S. Cl.
CPC . *A61J 1/10* (2013.01); *C12M 35/04* (2013.01); *C12M 23/14* (2013.01); *B01L 3/5021* (2013.01); *B01L 3/505* (2013.01); *C12N 15/87* (2013.01)
USPC ...... 435/455; 435/69.1; 435/70.1; 435/283.1; 435/289.1; 435/320.1; 435/325; 435/383; 435/384

(58) Field of Classification Search
None
See application file for complete search history.

(56) References Cited

U.S. PATENT DOCUMENTS

| | | | |
|---|---|---|---|
| 4,142,670 A | | 3/1979 | Ishimaru et al. |
| 4,316,576 A | | 2/1982 | Cullis et al. |
| 4,909,949 A | * | 3/1990 | Harmony et al. ............. 210/787 |
| 5,648,251 A | | 7/1997 | Kotani et al. |
| 6,221,666 B1 | * | 4/2001 | Clarke et al. .................. 435/459 |
| 6,787,359 B1 | | 9/2004 | Ueno et al. |
| 2002/0173034 A1 | * | 11/2002 | Barbera-Guillem et al. . 435/325 |
| 2004/0132177 A1 | | 7/2004 | Heron |
| 2006/0068369 A1 | | 3/2006 | Coelho et al. |
| 2009/0011485 A1 | | 1/2009 | Chono et al. |
| 2009/0162936 A1 | | 6/2009 | Marui et al. |

FOREIGN PATENT DOCUMENTS

| | | |
|---|---|---|
| JP | 2000-504942 A2 | 4/2000 |
| JP | 2002335950 | 11/2002 |
| JP | A-2004-201689 A | 7/2004 |
| JP | 2006-174852 A | 7/2006 |
| WO | 9524464 A1 | 9/1995 |
| WO | 98/07829 A1 | 2/1998 |
| WO | 9807829 A2 | 2/1998 |
| WO | 00/01836 | 1/2000 |
| WO | 0018636 A1 | 1/2000 |
| WO | 2006082958 A1 | 10/2006 |
| WO | 2006134871 A1 | 12/2006 |
| WO | 2008023771 A1 | 2/2008 |

OTHER PUBLICATIONS

Springer et al. "Gene Delivery to Muscle." Current Protocols in Human Genetics, John Wiley & Sons, Inc. 2001, pp. 13.4.1-13.4.19.*
Lamers et al., "Protocol for gene transduction and expansion of human T lymphocytes for clinical immunogene therapy of cancer" 9 Cancer Gene Therapy 613-623 (2002).*
J-T Lee et al., Engineering the Splice Acceptor for Improved Gene Expression and Viral Titer in an MLV-Based Retroviral Vector, Gene Therapy, (2004), vol. 11, pp. 94-99.
Sally McTaggart et al., Effects of Culture Parameters on the Production of Retroviral Vectors by a Human Packaging Cell Line, Biotechnol., (2000), vol. 16, pp. 859-865.
LCM Kaptein et al., Optimized Conditions for the Production of Recombinant Amphotropic Retroviral Vector Preparations, Gene Therapy, (1997), vol. 4, pp. 172-176.
Office Action issued in corresponding Japanese Patent Application No. 2006-227118, mailed Feb. 7, 2012, and English translation thereof.
Supplementary European Search Report in corresponding European appl. No. 07086012, dated Oct. 5, 2012.

* cited by examiner

*Primary Examiner* — Celine Qian
*Assistant Examiner* — Nancy J Leith
(74) *Attorney, Agent, or Firm* — Browdy and Neimark, PLLC (57) ABSTRACT

The present invention provides a baglike container for centrifugation that is mounted in a centrifuge to thereby allow centrifugation of a dispersion liquid accommodated therein. The baglike container for centrifugation is less likely to tear or break as a result of centrifugation by disposing a container wall surface of the baglike container so as to apply centrifugal force perpendicular to the container wall surface.

12 Claims, 2 Drawing Sheets

BAGLIKE CONTAINER FOR CENTRIFUGATION AND METHOD OF GENE TRANSFER USING THE SAME

TECHNICAL FIELD

The present invention relates to a baglike container for centrifugation that is mounted in a centrifuge to thereby allow centrifugation of any liquid dispersion accommodated therein, and is less likely to result in bag tearing or breakage upon centrifugation, and a method of gene transfer using the baglike container. More particularly, the present invention relates to a baglike container for centrifugation that is less likely to result in bag tearing or breakage upon centrifugation by disposing a container wall surface of the baglike container in parallel to a floor face of an adapter of a centrifuge so as to apply a centrifugal force perpendicular to the container wall surface, and a method of gene transfer using the baglike container.

BACKGROUND ART

A baglike container has conventionally been used so as to transfer, mix or separate a liquid pharmaceutical or solution. For example, a so-called soft bag, that is a baglike container containing a medicinal liquid for administering an intravenous drip to a patient, is used as a container for a drip. A so-called double bag is also used that is a baglike container in which two or more kinds of medicinal liquids are separately sealed in one baglike container having at least one partition so that the partition is broken immediately before use and the medicinal liquids are mixed and then intravenously fed as a drip to the patient. There is also a blood bag including a plurality of baglike containers in which collected blood is separated into respective components and accommodated in a plurality of containers, and then the separated components can be administered to another case patient.

In addition, this kind of baglike container is variously employed so as to handle a liquid pharmaceutical or solution. The reason is as follows. Namely, since an internal volume of a baglike container can vary according to the amount of a content liquid, it is necessary to promote filling and discharge of the content liquid by discharging air in the container or feeding air into the container when filling or discharging the content liquid. However, the container described above has a feature that it can fill or discharge the content liquid trough an attached port or a tube connected to the port. This feature makes it easy to realize a so-called closed system that enables execution of the above operation without causing contact of the content liquid with the open air, namely, execution of the operation without contamination of the content liquid with microorganisms from the open air. Therefore, this kind of the container is suited for use as a container for handling a liquid pharmaceutical collected and produced aseptically.

For these reasons, it is often preferred to employ a baglike container as a container which is required to have sterility. A baglike container is also employed as a container required to have sterility and requiring a centrifugal operation. The blood bag is one example thereof.

Namely, the blood bag as a baglike container filled with blood, as a dispersion liquid in which dispersoids such as red blood cells, white blood cells and blood platelets are dispersed in a dispersion medium such as blood plasma, is centrifuged to thereby separate blood in the container into components such as red blood cells, white blood cells, blood platelets and blood plasma, that are then transferred to and filled into separate baglike containers and then administered on a component to component basis to a plurality of patients.

Since the blood bag is used for the purpose of separating and recovering each component of the dispersion liquid, centrifugation is conducted by disposing a baglike container containing blood as the dispersion liquid, in a lengthwise centrifugal cup having a small floor area, with the port side upward and the bottom side downward.

In such a case, the container wall located under the liquid level formed on the surface of the dispersion liquid by a centrifugal force closely adheres to the inner face of a centrifugal adapter and does not further expand outwardly. As a result, tension is scarcely generated along the wall surface of the container wall and thus bag tearing and pinholes are not easily caused by centrifugation.

However, when a container is required to have sterility and requires a centrifugal operation, and is used for the purpose of not only separating the dispersion liquid into each component through centrifugation, for example, but also introducing a gene into target cells, dispersoids such as target cells and a vector are sedimented by centrifugation so as to be uniformly dispersed on a floor face of the container to thereby provide an environment that facilitates contact between the target cells and the vector, and, thus, a gene transfer efficiency is improved (see, for example, Patent Documents 1 and 2). A small floor area causes stacking of target cells upon centrifugation or contacting, which leads to a poor contact efficiency between the target cells and the vector and a poor gene transfer efficiency. Therefore, it is necessary to increase the floor area so that target cells can coexist in the uniform and scattered state without stacked on the floor face.

By conducting this operation on a floor face coated with a protein having high affinity for both the target cells and the vector, a contact efficiency between the target cells and the vector can be improved and also a gene transfer efficiency can be improved. Also in this case, when target cells become stacked, some cells cannot be contacted with the floor face coated with a protein, which leads to a poor gene transfer efficiency. Therefore, it is necessary to increase the floor area so that the target cells are dispersed without stacked on the floor face.

In order for a baglike container to satisfy these conditions during centrifugation, there is conducted an operation that a baglike container is laid on an adapter of a centrifuge having a large floor area, namely, a container wall surface of the baglike container is disposed in parallel to a floor face of the same adapter and centrifugation is conducted so as to apply a centrifugal force perpendicular to a container wall surface.

As a matter of course, when the container wall surface of the baglike container is coated with a protein having high affinity for both the target cells and the vector, the baglike container is disposed so that the protein-coated container wall surface of the baglike container functions as the floor face upon centrifugation.

Upon such the centrifugation, a centrifugal force to be applied on a content liquid in the baglike container, namely a culture medium, is converted into a pressure, while a force is produced expanding the container wall of the baglike container in the direction perpendicular to the floor face. However, it is impossible to expand the container wall of the baglike container in the direction perpendicular to the floor face as a result of obstruction with the floor face by the adapter. In contrast, a force capable of expanding in the direction parallel to the floor face is generated and thus both sides of the baglike container are exposed to a pressure load. Usually, this portion corresponds to the seal portion of the baglike container and may result in bag tearing as a result of seal peeling or breakage upon sealing. In particular, when only a weak seal strength is obtained like the case of sealing container walls each being composed of a different material, bag tearing may arise more easily.

In a baglike container containing cells requiring proliferation or activation during or after a centrifugal operation, culturing performance may be further improved, in some cases, by using different materials in the container wall of the floor face and the container wall of the ceiling. In this case, since different materials produce a seal, a seal having a strong seal strength is not necessarily obtained.

For example, this includes, the case where a material having affinity for cells is selected as a material constituting the container wall of the floor face, and a material having gas permeability is selected as a material constituting the container wall of the ceiling.

[Patent Document 1] U.S. Pat. No. 5,648,251
[Patent Document 2] International Publication No. WO 00/01836

DISCLOSURE OF THE INVENTION

Problems to be Solved by the Invention

An object to be achieved by the present invention is to provide a baglike container for centrifugation that can realize a closed system which does not cause microbial contamination during filling or discharge of a content liquid, and which is easy to handle, and a method of gene transfer using the baglike container.

Another object of the present invention is to provide a baglike container for centrifugation that does not easily result in bag tearing even when a container wall surface is disposed in parallel to a floor face of an adapter of a centrifuge formed perpendicular to a centrifugal force during centrifugation and centrifugation is conducted so as to apply a centrifugal force perpendicular to the container wall surface, and a method of gene transfer using the baglike container.

Still another object of the present invention is to provide a baglike container for centrifugation that has a large enough floor area to result in no stacking of sedimented dispersoids even when dispersoids in a dispersion liquid are sedimented by a centrifugal force upon centrifugation, and a method of gene transfer using the baglike container.

A further object of the present invention is to provide a baglike container for centrifugation that allows for easy observation of the state of a dispersion liquid, a dispersoid and a dispersion medium before centrifugation, and the sedimented dispersoid after centrifugation using an inverted microscope, and a method of gene transfer using the baglike container.

A still further object of the present invention is to provide a baglike container for centrifugation that can efficiently introduce a gene into target cells by utilizing a centrifugal force while maintaining proliferation properties and activity of target cells, and a method of gene transfer using the baglike container.

A still further object of the present invention is to provide a baglike container for centrifugation that has satisfactory proliferation efficiency which enables continuous culturing without transferring to another container after a gene transfer operation utilizing a centrifugal force, and a method of gene transfer using the baglike container.

Means to Solve the Problems

The baglike container for centrifugation according to claim 1 of the present invention is a baglike container for centrifugation that is mounted in a centrifuge to thereby allow centrifugation of a dispersion liquid accommodated therein, the baglike container for centrifugation including:

a main frame constituted of a first container wall with a recess portion formed so as to allow mounting in the centrifuge and with a flange portion provided on a periphery surrounding an aperture of the recess portion, and a flexible second container wall having its peripheral portion sealed mutually with the flange portion of the first container wall so as to define a storing space for storing the dispersion liquid in cooperation with the recess portion, and a port mounted in the main frame so as to be in communication with the storing space, wherein the recess portion defining the storing space can be set in the centrifuge so as to apply a centrifugal force perpendicular to the bottom plane of the recess portion.

Namely, the baglike container for centrifugation according to embodiment 1 of the present invention allows mounting of one of container walls of the baglike container in a centrifuge, and also allows increasing of an area of the bottom plane to which a centrifugal force is perpendicularly applied upon centrifugation, and thus making it possible to widely disperse dispersoids in a dispersion liquid, that are to be sedimented upon centrifugation, on the bottom plane without being concentrated at a specific position in the container, and to prevent application of an excess pressure to a sealed edge having a poor strength caused by a pressure generated in the dispersion liquid upon centrifugation.

The reason why an excess pressure upon centrifugation is not applied to the sealed edge will now be simply described.

Since a centrifugal force is applied in the direction perpendicular to the bottom plane of the recess portion upon centrifugation, the dispersion liquid in the recess portion does not flow out over the flange portion. Namely, the dispersion liquid accommodated in the recess portion does not exert an adverse influence causing breakage of the sealed edge formed at the flange portion, thereon.

The pressure exerting an adverse influence causing breakage of the sealed edge is generated when the dispersion liquid exceeds the capacity of the recess portion. Since this pressure is in proportion to the depth to the sealed edge from the liquid level upon centrifugation, the sealed edge is located at a lower level than the liquid level upon centrifugation. Furthermore, as compared with a common baglike container that is most likely to be located at the same depth as that of the bottom plane, the pressure to be applied to the sealed edge can be remarkably decreased in the baglike container of the present invention.

In order to exert no adverse influence on the sealed edge, the amount of the dispersion liquid may be controlled to the capacity that is less than that of the recess portion. When the dispersion liquid flows out over the sealed edge because of a curved surface formed on the surface of the dispersion liquid upon centrifugation, a presser panel for covering the flange portion can be used so as to prevent the dispersion liquid from flowing out over the sealed edge. The presser panel is preferably formed of a plastic.

Although the material constituting a first container wall may be a resin, the resin may be a hard or soft resin and conventional resins can be used. For example, the material is selected from a polyethylene-based resin, a polypropylene-based resin, a cycloolefin-based resin, a styrene-based resin, a polybutadiene-based resin, and a copolymer resin or mixture containing polymer components thereof. The first container wall may be formed of a composite sheet made of a mixture of resins described above. The composite sheet as used herein refers to a sheet formed of a plurality of resins, for example, a sheet formed of a resin mixture, a laminate film, a resin-coated resin film and a resin-printed resin film.

Since a cycloolefin resin is a resin that hardly exerts an adverse influence on the human body or cells, at least a portion of the inside plane of the first container wall is preferably formed of the cycloolefin resin.

When the baglike container of the present invention is used for an application that requires observation of the dispersion liquid accommodated in the container, especially an application where the dispersion liquid is observed with an inverted microscope, at least the bottom plane of the recess portion is preferably transparent.

Furthermore, the material constituting a flexible second container wall is selected from flexible resins, for example, a polyethylene-based resin, a polypropylene-based resin, a cycloolefin-based resin, a styrene-based resin, a polybutadiene-based resin, and a copolymer resin or mixture containing polymer components thereof taking account of flexibility and gas permeability. Similar to the first container wall, the second container wall may be formed of a composite sheet made of a mixture of resins described above.

The port can also be formed of a resin, and the resin is selected from a polyethylene-based resin, a polypropylene-based resin, a cycloolefin-based resin, a styrene-based resin, a polybutadiene-based resin, and a copolymer resin or mixture containing polymer components thereof taking account of adherence and adherability with the first container wall and the second container wall.

When the dispersion liquid to be accommodated in the container of the present invention contains living cells associated with cell culture or gene transfer, at least one of the first and second container walls preferably has gas permeability.

The depth of the recess portion of the first container wall is preferably 3 mm or more. When the depth is less than 3 mm, there is a problem that since the container has too small capacity as compared with the size of the container, an efficiency is remarkably deteriorated, being not preferable.

The expression "the centrifugal force is applied perpendicular to the bottom plane" as used herein does not necessarily mean that the centrifugal force is applied perpendicular to the entire bottom plane, but means that the centrifugal force is applied perpendicular at least to the main portion or the center portion of the bottom plane, or the portion in the vicinity thereof.

The above-described flexibility of the second container wall means follow-up ability of the container wall that it is deformable to such an extent that the dispersion liquid can flow in or out of the container without ingress and egress of air, while ensuring the volume of the recess portion of the first container wall. This follow-up ability does not vary depending only on the physical numerical value of the material constituting the container wall, but also varies depending on the form of the container and the amount of air existing in the container. Therefore, it is not proper to unconditionally limit by the physical numerical value of the material constituting the container wall.

Taking account of the applicable field of the present invention, flexibility as used herein may be flexibility that enables a requisite amount of the dispersion liquid to nearly entirely flow in or out under a pressure drop, for example about a 50 cm column of water, under the state where a proper amount of air exists in the container.

Since the above performance is not limited to the performance of only one container wall and influence is exerted by flexibility of the opposite other container wall, flexibility of one container wall should be generally judged taking account of flexibility of the other one.

The invention according to claim 2 is characterized in that, in addition to the constitution according to embodiment 1, the bottom plane of the recess portion is formed as a single plane over the entire region, and the depth from the flange portion to the bottom plane of the recess portion is 50% or less of a square root of an area of the bottom plane of the recess portion.

In the baglike container for centrifugation according to embodiment 2, since the bottom plane of the recess portion is formed as a single plane over the entire region, the amount of the dispersion liquid per unit area of the bottom plane is uniform over the entire bottom plane and the sediment can be uniformly dispersed. The flange portion preferably has a plane in parallel to the bottom plane of the recess portion since larger filling capacity can be ensured as compared with the capacity of the recess portion.

The entire region of the bottom plane as used herein does not include the chamfer portion formed at the corner of the recess portion.

The plane as used herein includes not only a plane having an infinite radius of curvature, but also a flat plane having a radius of curvature that exerts substantially the same effect. In addition, a plane having the same curvature as that of the liquid level of the dispersion liquid upon centrifugation is also included.

This plane may be subjected to sand treatment or emboss treatment.

By controlling the depth to the bottom plane of the recess portion from the flange portion to 50% or less of a square root of the area of the bottom plane, namely, decreasing the depth to the bottom plane from the liquid level upon centrifugation, or increasing the area of the bottom plane, small dispersoids can be sedimented within a short time without stacking sediments over each other.

The depth to the bottom plane from the flange portion is more preferably 30% or less of a square root of the area of the bottom plane taking account of the production of the container of the present invention.

The invention according to embodiment 3 is characterized in that, in addition to the constitution according to embodiment 1 or 2, the second container wall has a protruding portion that can be accommodated in the recess portion of the first container wall.

In the baglike container for centrifugation according to embodiment 3 of the present invention, by providing the second container wall with a protruding portion that can be accommodated in the recess portion of the first container wall, the protruding portion of the flexible second container wall can be largely deformed upon filling and discharge of the dispersion liquid and thus ensures and facilitates accommodation and discharge of the dispersion liquid.

Even in the case of a baglike container, for example, an infusion solution bag, a minimum volume of a storing space of the infusion solution as the material to be accommodated is more than 0 ml. Since the infusion solution cannot be completely discharged by accommodating only the infusion solution in the bag, a slight amount of air is usually placed together with the infusion solution. Specifically, by placing air in the amount of 10 to 15% of the infusion solution to be filled, dischargeability is maintained.

In the baglike container for centrifugation of the present invention, a minimum volume of the space, in which the dispersion liquid as the material to be accommodated, is preferably within 15% of the volume of the recess portion.

The minimum volume as used herein is a volume of the space occupied by the liquid remaining in the storing space when the storing space is filled with a liquid and the liquid is discharged only by a force resulting from a fall in pressure.

The invention according to embodiment 4 is characterized in that, in addition to the constitution according to any one of embodiments 1 to 3, the dispersion liquid is a dispersion liquid containing a vector and/or target cells dispersed therein as a dispersoid.

Namely, according to the baglike container for centrifugation of the present invention, by accommodating a dispersion liquid containing a vector and/or target cells as dispersoids dispersed therein followed by centrifugation, a gene can be efficiently introduced into target cells via the vector.

There is no specific limitation of the vector and examples thereof include non-virus vectors (liposomes, etc.) having an ability capable of introducing a nucleic acid into cells, and virus vectors such as retrovirus vector (including lentivirus vector, pseudo-type vector), adenovirus vector and adeno-associated virus vector.

The invention according to embodiment 5 is characterized in that, in addition to the constitution according to any one of embodiments 1 to 4, the bottom plane of the recess portion is coated with a material capable of holding a vector and/or target cells.

Namely, according to the baglike container for centrifugation according to embodiment 5 of the present invention, the bottom plane of the recess portion is coated with a material to which a vector and/or target cells is/are easily adhered, frequency of contact between the vector and target cells is increased using a gene transfer method, and thus gene transfer is efficiently conducted.

The material capable of holding the vector and/or target cells includes a component constituting an extracellular matrix, a derivative thereof, or a fragment thereof, and is preferably fibronectin, laminin, collagen, proteoglycan, or a fragment thereof. Furthermore, virus affinitive materials such as polylysine and DEAE-dextran, antiviral antibodies, and anti-target cell antibodies can also be used. These materials may be used alone or in combination.

When a fibronectin fragment CH-296 (RetroNectin (trade name), manufactured by TAKARA BIO INC.) is used as the fragment, it becomes possible to efficiently conduct gene transfer particularly when using a retrovirus vector.

The invention according to embodiment 6 is a method of gene transfer, using a baglike container for centrifugation having:

a main frame constituted of a first container wall with a recess portion formed so as to allow mounting in the centrifuge and with a flange portion provided on a periphery surrounding an aperture of the recess portion, and a flexible second container wall having its peripheral portion sealed mutually with the flange portion of the first container wall so as to define a space for storing the dispersion liquid in cooperation with the recess portion, and a port mounted in the main frame so as to be in communication with the storing space, the method comprising:

a first step of accommodating a dispersion liquid containing a vector and/or target cells dispersed therein as a dispersoid in the storing space, a second step of setting the baglike container in a centrifuge so as to apply a centrifugal force perpendicular to the bottom plane of the recess portion of the baglike container, and a third step of applying a centrifugal force to the dispersion liquid.

Namely, according to the method of gene transfer according to embodiment 6 of the present invention, a dispersion liquid containing a vector or target cells as dispersoids dispersed therein is accommodated in a storing space in the baglike container for centrifugation having the above-described features and performance with respect to the invention according to embodiment 1 and the baglike container is mounted in a centrifuge so as to apply a centrifugal force perpendicular to the bottom plane of the recess portion, and thus the centrifugal force is applied to a dispersion liquid to increase a gene transfer efficiency.

Examples of the case employing the step of the present invention as a portion of the step of the method of gene transfer include:

1. A case in which a vector as a contents material is accommodated in the baglike container for centrifugation, followed by centrifugation, and then target cells are accommodated;
2. A case in which a vector as a contents material is accommodated in the baglike container for centrifugation, followed by centrifugation, and then target cells are accommodated, followed by further centrifugation;
3. A case in which a vector and target cells as a contents material are accommodated in the baglike container for centrifugation, followed by centrifugation;
4. A case in which target cells as a contents material are accommodated in the baglike container for centrifugation, followed by centrifugation, and then a vector is accommodated; and
5. A case in which target cells as a contents material are accommodated in the baglike container for centrifugation, followed by centrifugation, and then a vector is accommodated, followed by centrifugation.

All cases are included in the scope of the present invention.

In the above cases 1, 2, 4 and 5, by discharging only a dispersion medium of the contents material after accommodating the vector (cases 1, 2) or target cells (case 4, 5) followed by centrifugation, a culture medium or a buffer solution may be replaced. Furthermore, the vector or cells can also be washed by adding a new culture medium or buffer solution, followed by discharge.

In the case of introducing a gene, it is preferred that the vector or target cells may be uniformly dispersed and sedimented on the bottom plane of the recess portion without causing stacking, as described above with respect to the invention according to embodiment 1 since the gene transfer effect is improved. Therefore, the bottom plane of the recess portion preferably has a large area.

The invention according to embodiment 7 is characterized in that, in addition to the constitution according to embodiment 6, wherein the bottom plane of the recess portion is formed as a single plane over the entire region, and the depth from the flange portion to the bottom plane of the recess portion is 50% or less of a square root of an area of the bottom plane of the recess portion.

It is preferred that the flange portion has a plane in parallel to the bottom plane of the recess portion since a larger filling capacity can be ensured relative to the capacity of the recess portion.

Advantages obtained from the baglike container for centrifugation to be used in the method of gene transfer according to embodiment 7 are as described with respect to the container of the invention according to embodiment 2.

The invention according to embodiment 8 is characterized in that, in addition to the constitution according to embodiment 6 or 7, the second container wall has a protruding portion capable of being accommodated in the recess portion of the first container wall.

Advantages obtained from the baglike container for centrifugation to be used in the method of gene transfer according to embodiment 8 are as described with respect to the container of the invention according to embodiment 3.

The invention according to embodiment 9 is characterized in that, in addition to the constitution according to any one of embodiments 6 to 8, the bottom plane of the recess portion is coated with a material capable of holding a vector and/or target cells.

Advantages obtained from the baglike container for centrifugation to be used in the method of gene transfer according to embodiment 9 are as described with respect to the container of the invention according to embodiment 5.

The invention according to embodiment 10 is characterized in that, in addition to the constitution according to embodiment 9, the first step is a step of accommodating a dispersion liquid containing a vector dispersed therein as a dispersoid in the storing space of the baglike container for centrifugation, and the method of gene transfer further comprises a fourth step of accommodating target cells in the storing space so as to bring into contact with the vector after adhering or fixing the vector to a material capable of holding the vector coated on the bottom plane of the recess portion by the centrifugal force applied in the third step.

Since the method of gene transfer according to embodiment 10 can adhere a vector to the material capable of holding the vector coated on the bottom plane of the container by a centrifugal operation with a high efficiency, for example, it becomes possible to remove a component which inhibits gene transfer included in the dispersion liquid containing the vector, by discharging the dispersion medium, and thus the method is useful for improving a gene transfer efficiency.

Effect of the Invention

As described above, according to the present invention, there can be provided a baglike container for centrifugation that can realize a closed system which does not cause microbial contamination in filling or discharge of a dispersion liquid, and is easy to handle, and a method of gene transfer using the baglike container.

It is also possible to provide a baglike container for centrifugation that does not easily result in bag tearing even when fitted in a centrifuge so as to apply a centrifugal force perpendicular to the bottom plane of a recess portion, and a method of gene transfer using the baglike container for centrifugation.

It is also possible to provide a baglike container for centrifugation that has a large enough floor area to result in no stacking of sedimented dispersoids even when dispersoids in a dispersion liquid are sedimented by a centrifugal force upon centrifugation, and a method of gene transfer using the baglike container.

It is also possible to provide a baglike container for centrifugation that allows for easy observation of the state of a dispersion liquid, a dispersoid and a dispersion medium before centrifugation, and the sedimented dispersoid after centrifugation using an inverted microscope, and a method of gene transfer using the baglike container.

It is also possible to provide a baglike container for centrifugation that can efficiently introduce a gene into target cells by utilizing a centrifugal force while maintaining proliferation properties and activity of target cells, and a method of gene transfer using the baglike container.

It is also possible to provide a baglike container for centrifugation that has a satisfactory proliferation efficiency which enables continuous culturing without transferring to another container after a gene transfer operation utilizing a centrifugal force, and a method of gene transfer using the baglike container.

The baglike container for centrifugation of the present invention is not limited to the case of centrifugation and can also be merely used as a closed culturing container with satisfactory operability, although particularly large effect is expected when centrifugation is conducted as described above.

DESCRIPTION OF REFERENCE NUMERALS

1: Baglike container
2: Peripheral seal
3: First container wall
4: Second container wall
5: Port
6: Recess portion of first container wall
6': Content storing space
7: Flange portion of first container wall
8: Cap
9: Hanging hole
10: Protruding portion of second container wall
11: Dispersion liquid

BEST MODE FOR CARRYING OUT THE INVENTION

Embodiments of the present invention will now be described based on Examples with reference to the accompanying drawings.

Example 1

Figure 1:
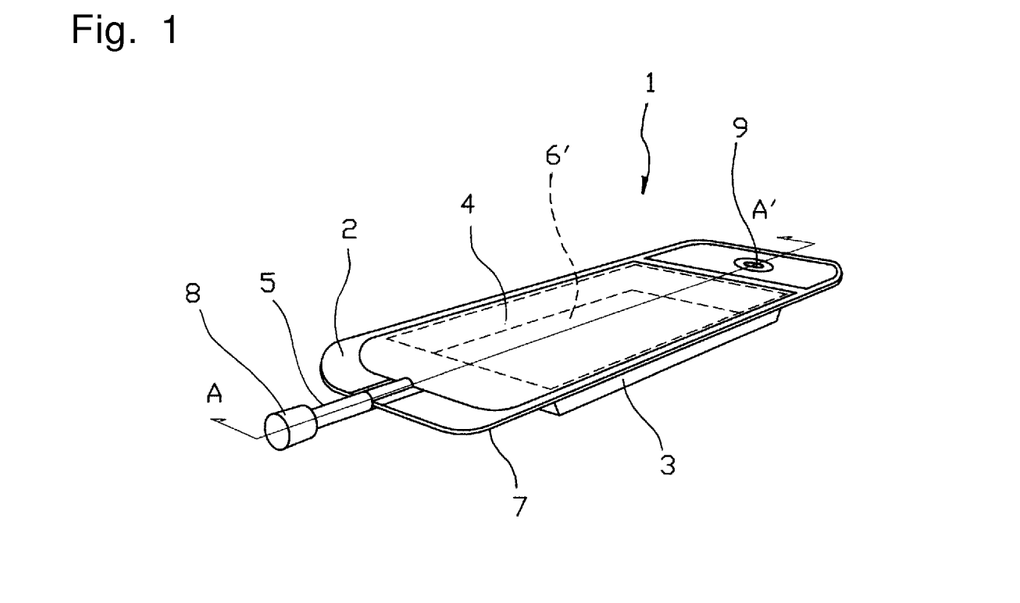
FIG. 1 is a perspective view showing an example of a baglike container of the present invention.
Figure 2:
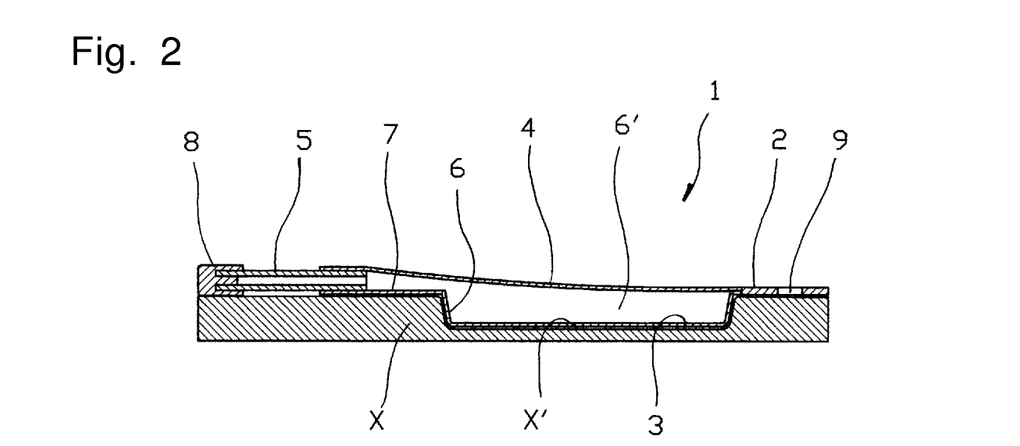
FIG. 2 is a schematic sectional view cut along line A-A' included in a perpendicular plane of the baglike container of FIG. 1.

As shown in FIG. 1 and FIG. 2, a baglike container 1 for centrifugation of the present Example is a container including opposing two container walls each having the periphery sealed with a peripheral seal 2, namely, a first container wall 3 and a second container wall 4, and a generally tubular port 5 used for filling a content liquid in a storing space 6' described hereinafter, or discharging the content liquid from the storing space 6'. The first container wall 3 includes a recess portion 6 and a flange portion 7 formed at the periphery of the recess portion 6, while the second container wall 4 is formed of a flexible material. As described above, by sealing the first container wall 3 and the second container wall 4 using the peripheral seal 2, the storing space 6' is defined by the recess portion 6 of the first container wall 3 and the second container wall 4.

Furthermore, a cap 8 is engaged with the external end of the port 5 for sealing the baglike container 1 for centrifugation, and the peripheral seal portion opposite to the peripheral seal portion of the container provided with the port 5 is provided with a hanging hole 9 for suspending the baglike container 1 for centrifugation of the present Example to serve to discharge a content liquid when the content liquid is to be discharged.

The first container wall 3 was made by forming a recess portion 6 having a length of 100 mm, a width of 60 mm and a depth of 9 mm by vacuum molding so as to locate a cycloolefin resin layer on an inner side of the recess portion 6, namely, on a plane of an inner side of the container using a two-layered structure sheet composed of a 40 μm thick cycloolefin resin layer (ZEONEX (trade name), manufactured by ZEON CORPORATION) and a 170 μm thick low-density polyethylene resin layer formed by a multilayer extrusion molding method.

The second container wall 4 was formed as a 110 μm thick sheet by inflation molding using an ethylene-vinyl acetate copolymer (ULTRACENE (trade name), manufactured by TOSOH CORPORATION).

Then, the first container wall 3 and the second container wall 4 were laid one upon another and an inner end of the port 5 was inserted between these container walls. Three parts were heat-sealed to thereby integrally seal the peripheral portion of the first container wall 3, the peripheral portion of the second container wall 4 and the inner end of the port 5, and then the unnecessary portion was trimmed to form a baglike container 1 for centrifugation of the present Example.

Fusion of the port 5 can also be conducted before or after peripheral sealing.

The baglike container 1 for centrifugation of the present Example was evaluated by the following methods for evaluation 1 to 3 to obtain the following results.

1. Filling and discharge could be conducted without ingress and egress of air.
2. Damage of the container was not recognized after repeated use.
3. It was recognized that K562 cells are uniformly sedimented on the bottom plane of a container.

Method for Evaluation

1. Evaluation of Flexibility of Container

Fifty milliliter of water was filled in a baglike container 1 for centrifugation of the Example and discharged. It was confirmed whether or not water can be discharged without ingress and egress of air.

After preliminarily decreasing the amount of air remaining in the baglike container 1 for centrifugation of the present Example by appropriately denting a second container wall 4 depending on the form of the container, or injecting a fixed amount of air in the baglike container 1 for centrifugation of the present Example, the above operation was conducted.

2. Evaluation of Damageability of Sealed Edge

This evaluation was carried out using a centrifuge equipped with an adapter provided with a recess portion having an inside dimension that is slightly larger than an external dimension of a recess portion 6 of a container 1. Describing in more detail, after filling 30 ml of water in the baglike container 1 for centrifugation of the present Example, as shown in FIG. 2, the container 1 was set in an adapter X by fitting the recess portion 6 of the container 1 into a recess portion X' of the adapter X of the centrifuge, and a centrifugal force was loaded to the baglike container 1 for centrifugation and the content by centrifugation under 1,000 g for 2 hours. Then, the damage state of the container was observed. Next, 5 ml of water was added to the container to a liquid amount of 35 ml and a centrifugal force was loaded to the baglike container 1 for centrifugation and the content liquid by centrifugation under 1,000 g for 2 hours. Then, the damage state of the container was observed. Next, 5 ml of water was further added to the container to a liquid amount of ml and a centrifugal force was loaded to the baglike container 1 for centrifugation and the content liquid by centrifugation under 2,000 g for 2 hours. Then, the damage state of the container was observed.

3. Evaluation of Dispersibility of Dispersoids to be Sedimented

In a baglike container 1 for centrifugation of the Example, 40 ml of a dispersion liquid, as a content liquid, prepared by dispersing K562 cells (ATCC CCL-243) in a 10% bovine fetal serum-containing RPMI1640 medium at a concentration of $1 \times 10^5$/ml was filled and this container was set in a recess portion X' of an adapter X, and then a centrifugal force was loaded to the baglike container 1 for centrifugation and the content liquid by centrifugation under 1,000 g for 15 minutes.

After completion of the centrifugation, the container was removed from the centrifuge so as to import little rotation or vibration as possible. With respect to 10 visual fields selected at random, the dispersed state of dispersoids of cells sedimented on the bottom plane of the container was observed using an inverted microscope.

Next, using the baglike container 1 for centrifugation of the present Example, target cells were subjected to a gene transfer operation by the following procedure and a gene transfer efficiency was measured.

1. Preparation of RetroNectin-Coated Container

A fibronectin fragment CH-296 (RetroNectin (trade name), manufactured by TAKARA BIO INC.) was diluted with PBS to 20 μg/ml, 10 ml of the resulting solution was injected into a baglike container 1 for centrifugation of the Example and allowed to stand at room temperature for 2 hours to coat the inner face of the container 1 with CH-296 and this was washed three times with 30 ml of PBS, followed by removal of the solution to obtain a RetroNectin-coated container.

2. Preparation of Retrovirus Vector

A retrovirus vector plasmid pMS-eGFP was made by the following procedure.

First, the 3'LTR region of a pMT vector [Gene Therapy, Vol. 11, pp. 94-99 (2004)] was substituted with MSCV LTR of pMSCVneo manufactured by Clontech Co. to make a plasmid vector pMS having MSCV LTR. A gene fragment of a green fluorescent protein gene eGFP was inserted into the multi-cloning site of pMS to obtain an eGFP-expressing recombinant retrovirus vector pMS-eGFP.

Using a pMS-eGFP vector and Retrovirus Packaging Kit Eco (manufactured by TAKARA BIO INC.), transient virus production in 293T cells was conducted to obtain an ecotropic MS-eGFP virus. GaLV retrovirus packaging cells PG13 (ATCC CRL-10686) were infected with the thus obtained ecotropic MS-eGFP virus in the presence of RetroNectin (manufactured by TAKARA BIO INC.) to obtain retrovirus-producing cells PG13/MS-eGFP. PG13/MS-eGFP was cultured in Dulbecco's Modified Eagle's Medium (DMEM, manufactured by SIGMA Co.) containing 10% bovine fetal serum (manufactured by GIBCO Co.). After grown until semiconfluent, the medium was replaced by 0.1 ml/cm² of a fresh serum-free culture medium GT-T-RetroI (manufactured by TAKARA BIO INC.). After 24 hours, the recovered culture supernatant was filtered through a 0.45 μm filter (manufactured by Millipore Corporation) to obtain a GALV/MS-eGFP virus liquid. The resulting virus liquid was subdivided, stored in a freezer at −80° C. and then subjected to the following gene transfer test.

3. Binding of Retrovirus Vector to RetroNectin-Coated Container

The retrovirus vector prepared in 2 was quickly thawed, diluted 8-fold with GT-T-RetroI. Then, 30 ml of the solution was filled in the RetroNectin-coated baglike container 1 produced in 1 and the container was set in a recess portion X' of an adapter X of a centrifuge, followed by centrifugation at 32° C. under 2,000 g for 2 hours. As a control, a 24-well non-treated plate was coated with RetroNectin and two groups in which 0.5 ml of the virus vector was added per well were prepared. One group among them was centrifuged at 32° C. under 2,000 g for 2 hours. The other one group was allowed to stand in a 5% $CO_2$ incubator at 37° C., for 4 hours to thereby bind the retrovirus vector.

4. Gene Transfer

With respect to the baglike container 1 for centrifugation, after completion of the centrifugation, the content liquid was discharged and washed with 30 ml of 1.5% HSA-containing PBS, and the washing solution was discharged. In a storing space 6' of the container 1 was filled 40 ml of a dispersion solution prepared by dispersing K562 cells in a 10% bovine fetal serum-containing RPMI1640 medium to concentration of $1.5 \times 10^4$/ml in advance, and this was allowed to stand in a 5% $CO_2$ incubator at a temperature of 37° C. to thereby conduct gene transfer into target cells. With respect to the 24-well plate, the content liquid was removed and washed with 0.5 ml of 1.5% HSA-containing PBS, and the washing solution was removed. To each well was added 0.5 ml of the K562 culture solution with $4 \times 10^4$/ml cells dispersed therein and this was allowed to stand in a 5% $CO_2$ incubator at a temperature of 37° C. to thereby conduct gene transfer into target cells. After culturing gene introduced-cells in each container for 3 days, cells were detached and recovered, and a gene transfer efficiency was measured using a flow cytometer. A relative value of a gene transfer efficiency in each container to a gene transfer efficiency in the case of using the 24-well plate while allowing to stand was calculated. The results are shown Table 1 below. As shown in Table 1 below, in the baglike container 1 for centrifugation of the present Example, a gene transfer efficiency was remarkably increased by binding the retrovirus vector to the container with a centrifugal force.

TABLE 1

| Gene transfer container | Relative value of gene transfer efficiency (%) |
| --- | --- |
| 24-well plate (allowed to stand) | 100.0 |
| 24-well plate (2,000 g) | 6908.6 |
| Baglike container for centrifugation (2,000 g) | 5464.9 |

5. Storage of Retrovirus Vector-Bound Container

With respect to the retrovirus vector-bound baglike container 1 for centrifugation produced in 3, after completion of the centrifugation, a content liquid was discharged, and replaced with 40 ml of 1.5% HSA-containing PBS, which was then stored at 4° C. for 24 hours and 48 hours. After storage, the liquid was discharged and 40 ml of a dispersion liquid prepared by dispersing K562 cells in a 10% bovine fetal serum-containing RPMI1640 medium $1.5 \times 10^4$/ml in advance was filled, and this was allowed to stand in a 5% $CO_2$ incubator at 37° C. to thereby conduct gene transfer into target cells. As a control, the retrovirus vector-bound baglike container 1 for centrifugation was immediately subjected to gene transfer without being stored at 4° C. By calculating a relative value of a gene transfer efficiency at each storage time to a gene transfer efficiency in a control, the gene transfer activity of the remaining retrovirus vector was calculated. The results are shown in Table 2 below. Usually, the retrovirus vector has poor stability and it is considered that the half life is 92 hours at 4° C., 18 to 64 hours at 0° C., 11 to 39 hours at 32° C., and 7 to 9 hours at 37° C. [McTaggart S., Al-Rubeai M., Biotechnol. Prog., Vol. 16, No. 5, pp. 859-865 (2000) (Non-Patent Document 1), Kaptein L. C. et al., Gene Ther., Vol. 4, No. 2, pp. 172-176 (1997) (Non-Patent Document 2)]. As shown in Table 2 below, the baglike container 1 for centrifugation, which is coated with RetroNectin, of the present Example is also suited for storage of the retrovirus vector.

TABLE 2

| Storage period | Relative value of activity of remaining retrovirus (%) |
| --- | --- |
| Control (not stored) | 100.0 |
| Stored at 4° for 24 hours | 99.7 |
| Stored at 4° for 48 hours | 87.9 |

Figure 3:
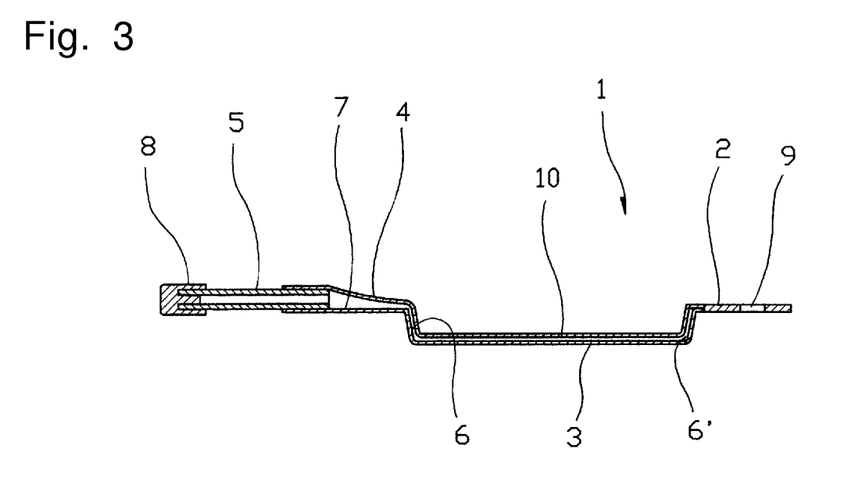
FIG. 3 is a schematic sectional view showing one example of the baglike container according to the present invention.
Figure 4:
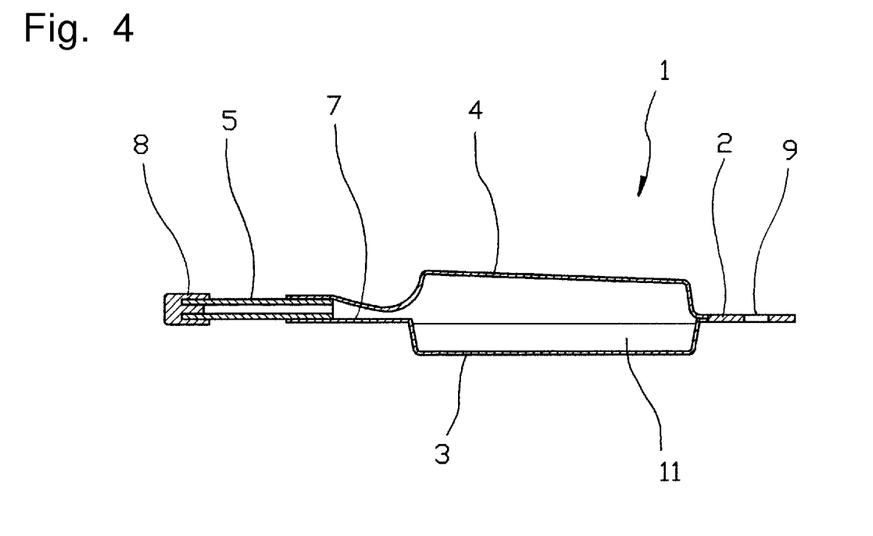
FIG. 4 is a schematic sectional view showing a state where a dispersion liquid is placed in the baglike container of FIG. 3.

According to the same manner as that of Example 1, a protruding portion 10 having an external dimension slightly smaller than an internal dimension of a recess portion 6 of a first container wall 3 was formed on a second container wall 4 by vacuum molding, the protruding portion 10 of the second container wall 4 was fitted in the recess portion 6 of the first container wall 3, and the periphery was sealed, in addition to the configuration of Example 1, as shown in FIG. 3 and FIG. 4, the baglike container 1 for centrifugation of the present Example was formed. The reference symbol 11 in FIG. 4 denotes a dispersion liquid.

The baglike container 1 for centrifugation of the present Example was evaluated in the same manner as in Example 1 and used for gene transfer in the same manner as in Example 1, and then a gene transfer efficiency was examined.

The baglike container 1 for centrifugation of the present Example was evaluated by the above methods of evaluation 1, 2 and 3. As a result, filling and discharge could be conducted without ingress and egress of air and the container was not damaged even after centrifugation, and also it was observed that dispersoids are uniformly dispersed on the bottom plane of the container.

INDUSTRIAL APPLICABILITY

As described above, the baglike container of the present invention allows uniform dispersion of dispersoids on the bottom plane upon centrifugation treatment without causing damage, and is therefore extremely useful as this kind of a container. Also, the method of gene transfer of the present invention using such the container allows efficient gene transfer and is therefore extremely useful.

The invention claimed is:

1. A baglike container for centrifugation that is mounted in an adapter of a centrifuge to thereby allow centrifugation of a dispersion liquid accommodated therein, said baglike container being a closed container, adapted for centrifugation, and comprising:
   a recess portion, having a bottom plane wall and side walls; and formed so as to allow mounting of the bottom plane wall in the centrifuge so as to prevent movement of the bottom plane wall, and with a flange portion provided on a periphery surrounding an aperture of the recess portion,
   a flexible second container wall which has (i) a peripheral portion sealed mutually with the flange portion surrounding the aperture of the recess portion so as to define a storing space for storing the dispersion liquid in cooperation with the recess portion and (ii) a protruding portion, the flexible second container wall being disposed directly opposite from the bottom plane wall of the recess portion, so that the dispersion liquid can be accommodated in the recess portion of the container, and a port mounted between the flexible second container and the flange portion so as to be in communication with the storing space, wherein the recess portion defining the storing space can be set in the centrifuge so as to apply a centrifugal force perpendicular to the bottom plane wall of the recess portion.

2. The baglike container for centrifugation according to claim 1, wherein the bottom plane wall is formed as a single plane, and the depth from the flange portion to the bottom plane wall is 50% or less of a square root of an area of the bottom plane wall.

3. The baglike container for centrifugation according to claim 1, wherein the dispersion liquid is a dispersion liquid containing a vector and/or target cells dispersed therein as a dispersoid.

4. The baglike container for centrifugation according to claim 1, wherein the bottom plane wall is coated with fibronectin fragment CH-296.

5. A method of gene transfer using a baglike container for centrifugation that is mounted in a centrifuge, comprising:

a first step of accommodating a dispersion liquid containing a vector and/or target cells dispersed therein as a dispersoid in the storing space of the baglike container for centrifugation of claim 1, a second step of setting the baglike container in a centrifuge so as to apply a centrifugal force perpendicular to the bottom plane of the recess portion of the baglike container, and a third step of applying a centrifugal force to the dispersion liquid.

6. The method of gene transfer according to claim 5, wherein, in the baglike container for centrifugation, the bottom plane of the recess portion is formed as a single plane over the entire region, and the depth from the flange portion to the bottom plane of the recess portion is 50% or less of a square root of an area of the bottom plane of the recess portion.

7. The method of gene transfer according to claim 5, wherein, in the baglike container for centrifugation, the second container wall has a protruding portion that can be accommodated in the recess portion of the first container wall.

8. The method of gene transfer according to claim 5, wherein, in the baglike container for centrifugation, the bottom plane of the recess portion is coated with a material capable of holding a vector and/or target cells.

9. The method of gene transfer according to claim 8, further comprising a fourth step of accommodating target cells in the storing space so as to bring into contact with the vector after adhering or fixing the vector to a material capable of holding the vector coated on the bottom plane of the recess portion by the centrifugal force applied in the third step.

10. The baglike container for centrifugation according to claim 1, wherein the bottom plane wall is capable of retaining its bottom plane shape upon centrifugation of the baglike container.

11. The baglike container for centrifugation according to claim 1, wherein said periphery surrounding the aperture of the recess portion has a plane parallel to the bottom plane of the recess portion.

12. The baglike container for centrifugation according to claim 1, which, upon centrifugation with cells in the container, is capable of uniformly sedimenting the cells on the bottom plane of said recess portion.

\* \* \* \* \*